(12) United States Patent
Pickett et al.

(10) Patent No.: US 10,334,845 B2
(45) Date of Patent: Jul. 2, 2019

(54) OLFACTORY LIGANDS

(71) Applicants: University College Cardiff Consultants Limited, Cardiff, South Glamorgan (GB); Rothamsted Research, Harpenden, Hertfordshire (GB)

(72) Inventors: John Anthony Pickett, Harpenden (GB); Michael Alexander Birkett, Harpenden (GB); David James Miller, South Glamorgan (GB); Rudolf Konrad Allemann, South Glamorgan (GB)

(73) Assignees: UNIVERSITY COELLEGE CARDIFF CONSULTANTS LIMITED, Cardiff, Wales (GB); ROTHAMSTED RESEARCH, Harpenden, Hertfordshire (GB)

( * ) Notice: Subject to any disclaimer, the term of this patent is extended or adjusted under 35 U.S.C. 154(b) by 2 days.

(21) Appl. No.: 15/542,097

(22) PCT Filed: Dec. 23, 2015

(86) PCT No.: PCT/GB2015/054139
§ 371 (c)(1),
(2) Date: Jul. 7, 2017

(87) PCT Pub. No.: WO2016/110671
PCT Pub. Date: Jul. 14, 2016

(65) Prior Publication Data
US 2018/0271089 A1  Sep. 27, 2018

(30) Foreign Application Priority Data
Jan. 9, 2015 (GB) .................................. 1500348.6

(51) Int. Cl.
*C12N 9/88* (2006.01)
*C12N 15/82* (2006.01)
*C12P 5/00* (2006.01)
*A01N 27/00* (2006.01)
*C07C 13/271* (2006.01)

(52) U.S. Cl.
CPC ............ *A01N 27/00* (2013.01); *C07C 13/271* (2013.01); *C12N 9/88* (2013.01); *C12P 5/002* (2013.01); *C12P 5/007* (2013.01); *C12Y 402/03075* (2013.01); *C07C 2601/18* (2017.05); *C07K 2319/21* (2013.01)

(58) Field of Classification Search
CPC ....... C12N 15/82; C12N 15/8286; C12P 5/00; C12P 5/007; C12Y 402/03075
See application file for complete search history.

(56) References Cited

FOREIGN PATENT DOCUMENTS

WO    2004/058814 A1    7/2004

OTHER PUBLICATIONS

Cascon et al. Aug. 15, 2012; Chemoenzymatic preparation of germacrene analogues. Chem. Commun. 48: 9702-9704, plus Electronic Supplementary Information pp. S1-S51.*
Touchet et al. Apr. 7, 2015; Novel olfactory ligands via terpene synthases. Chem. Commun. 51: 7550-7553, plus Electronic Supplementary Information pp. S1-S31.*
Search Report dated Jan. 19, 2016 of the Patent Office of Great Britain for Application No. GB1500348.6.
Written Opinion and Search Report of the International Search Authority dated Feb. 24, 2016 for International application No. PCT/GB2015/054139.
Prosser, et al., Enantiospecific (+)- and (i)-germacrene D synthases, cloned from goldenrod, reveal a functionally active variant of the universal isoprenoid-biosynthesis aspartate-rich motif; Archives of Biochemistry and Biophysics 432 (2004) 136-144.

* cited by examiner

*Primary Examiner* — Karen Cochrane Carlson
(74) *Attorney, Agent, or Firm* — King & Schickli, PLLC

(57) ABSTRACT

The invention provides analogs of (S)-germacrene D analog which have improved insect repellent properties compared to (S)-germacrene D analog or which have insect attractant properties.

26 Claims, 3 Drawing Sheets
Specification includes a Sequence Listing.

OLFACTORY LIGANDS

REFERENCE TO SEQUENCE LISTING SUBMITTED ELECTRONICALLY

A sequence listing electronically submitted with the present application as an ASCII text file named 1776-046SequenceListing_ST25.txt, created on Jul. 6, 2017 and having a size of 9490 bytes, is incorporated herein by reference in its entirety.

TECHNICAL FIELD

This application is the national stage of international patent application no. PCT/GB2015/054139 filed on Dec. 23, 2015 which in turn claims priority from British Patent Application No. 1500348.6 filed on Jan. 9, 2015, the disclosures of which are incorporated herein by reference in their entirety.

BACKGROUND

The ever increasing world population and subsequent growing demand for agricultural products requires progressively more efficient and improved plant breeding and crop protection methods. Crop pests, such as insects, result in significant reduction of yield and current pest control is reliant on the application of insecticides; however, the development of resistance to insecticides and their often negative impact on human health and the environment demands the development of appropriate and alternative compounds to those currently in use.

Semiochemicals are a class of substances which mediate intra- and interspecific communication between the same or different species. The process by which these signals are recognised is termed olfaction and is the process by which the olfactory signal or ligand is recognised by olfactory recognition proteins, resulting in a particular response. These olfactory recognition proteins are highly specific and capable of distinguishing even structurally related compounds. Semiochemicals are key recognition cues in perfumes and cosmetics or food and beverages, and have a role in the control of pests, particularly insects and are therefore highly sought after compounds. However, semiochemicals are usually extremely volatile, unstable compounds and their chemical synthesis is hugely expensive.

Terpenes and terpenoids are a large and diverse group of organic compounds commonly found in plants ranging from essential primary molecules to more complex secondary metabolites and are known for their semiochemical properties. Pesticide compounds and formulations that include terpenoids are disclosed in WO2013/191758. Terpenes and terpenoids are hydrocarbons assembled of isoprene subunits providing the carbon skeleton which then undergoes further modification. The early core steps in the terpenoid biosynthesis are well characterised utilising the primary building blocks isopentenyl diphosphate (IDP) and dimethylallyl diphosphate (DMADP) and leading to the synthesis of the terpenoid precursors geranyl diphosphate (GDP), farnesyl diphosphate (FDP) and geranylgeranyl diphosphate (GGDP). Terpenes are classified sequentially dependent on their number of isoprene subunits as hemiterpenes (one isoprene subunit), monoterpenes (two isoprene subunits), sesquiterpenes (three isoprene subunits), etc.

Although terpenes and terpenoids are an attractive target for synthetic modification and the modulation of their natural properties may lead to new medicinal and agrochemical compounds with improved and altered functions. The complexity of the hydrocarbon skeletons and the chemical instability of many terpenoids, particular those with semiochemicals properties, can present a difficult challenge to the synthetic chemist. Synthetic biology approaches have focused on the preparation of natural terpenoids utilising whole biochemical pathways in living organisms, or increasing endogenous terpenoid production in plants to repel or attract insects or other organism such as disclosed in US2014/0173771; however, possible substrates for enzymes involved in the terpenoid synthesis are limited in cells and does not result in the generation of modified terpenoids with altered properties.

Germacrene D is known to repel insects, particularly aphids such as the grain aphid (*Sitobion avenae*) and there is therefore interest in producing analogues of germacrene D which may have modified properties.

Cascón et al, in *Chem. Commun.,* 48, 9702-9704 (2012), have described the synthesis of various germacrene D analogues using fluorine and methyl modified FDPs as a substrate for (S)-germacrene D synthase (GDS). In particular, they synthesised 6-F, 14-F, 15-F and 14-methyl analogues.

However, these germacrene D analogues proved to have reduced activity compared with germacrene D.

SUMMARY

According to an aspect of the invention there is provided a (S)-germacrene D analogue of general formula (I):

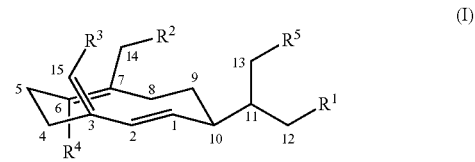

wherein
$R^1$ is H, methyl, ethyl, n-propyl, iso-propyl or cyclopropyl;
$R^2$ is H, methyl, ethyl, n-propyl, iso-propyl or cyclopropyl;
$R^3$ is methyl, ethyl, n-propyl, iso-propyl or cyclopropyl;
$R^4$ is H, methyl, ethyl, n-propyl, iso-propyl or cyclopropyl;
$R^5$ is H, methyl, ethyl, n-propyl, iso-propyl or cyclopropyl.

Cascón et al, (*Chem. Commun.,* 48, 9702-9704 (2012)) teach that it is not possible to synthesise compounds with a methyl group at the 15-position (i.e. the $R^3$ position in general formula (I) above). However, the present inventors have now successfully obtained compounds with a 15-substituent using a modification of the method described by Cascón et al and have found that they have particularly surprising properties.

Suitably in the compounds of general formula (I), $R^1$ is H, methyl or ethyl, more suitably H or methyl. Still more suitably, $R^1$ is H.

In the compounds of general formula (I), $R^2$ is suitably H, methyl or ethyl, more suitably H or methyl.

In the compounds of general formula (I), $R^3$ is methyl or ethyl and more suitably methyl.

Suitably in the compounds of general formula (I), $R^4$ is H, methyl or ethyl, more suitably H or methyl. Still more suitably, $R^4$ is H.

Suitably in the compounds of general formula (I), $R^5$ is H, methyl or ethyl, more suitably H or methyl. Still more suitably, $R^5$ is H.

Compounds of formula (I) in which R³ is methyl, ethyl, n-propyl, iso-propyl or cyclopropyl and R¹, R² and R⁴ are hydrogen are have insect repellent properties.

Therefore in some suitable compounds of general formula (I):
each of R¹, R² and R⁴ is H;
R³ is methyl, ethyl, n-propyl, iso-propyl or cyclopropyl; and
R⁵ is H, methyl, ethyl, n-propyl, iso-propyl or cyclopropyl.

More suitably, in such compounds, R⁵ is H, methyl or ethyl, especially H or methyl and particularly H.

Still more suitable compounds of general formula (I) are those in which:
each of R¹, R², R⁴ and R⁵ is H;
R³ is methyl or ethyl.

The compound of formula (I) in which R³ is methyl and R¹, R², R⁴ and R⁵ are hydrogen proved to have much greater insect repellent activity than the compounds synthesised by Cascón et al and therefore this compound is particularly suitable.

Other suitable compounds of formula (I) are those in which in which each of R², R³ and R⁵ is independently methyl, ethyl, n-propyl, iso-propyl or cyclopropyl and R¹ and R⁴ are H.

More suitably, in such compounds, R⁵ is H, methyl or ethyl, especially H or methyl and particularly H.

Still more suitable compounds of general formula (I) are those in which:
each of R¹, R⁴ and R⁵ is H;
each of R² and R³ is independently methyl or ethyl.

Surprisingly, the compound of general formula (I) in which R² and R³ are both methyl and R¹, R⁴ and R⁵ are hydrogen showed a reversal of activity, having strong insect attractant properties.

As discussed above, particularly suitable compounds of general formula (I) are those in which R³ is methyl and R¹, R², R⁴ and R⁵ are hydrogen ((S)-15-methylgermacrene D) or which R² and R³ are both methyl and R¹, R⁴ and R⁵ are hydrogen ((S)-14,15-dimethylgermacrene D).

Compounds of general formula (I) may be synthesised from a farnesyl diphosphate analogue of general formula (II):

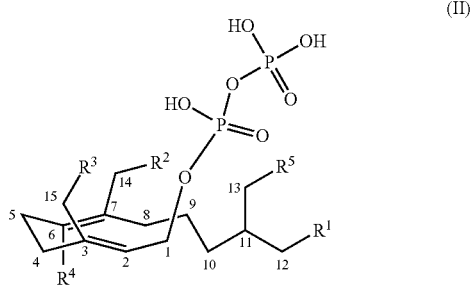

wherein R¹, R², R³, R⁴ and R⁵ are as defined in general formula (I);
or a salt thereof;
by incubation with germacrene D synthase (GDS).

Suitably the germacrene D synthase is a (S)-germacrene D synthase polypeptide which may be a recombinant polypeptide produced in any suitable organism, for example *E. coli*.

The recombinant GDS may comprise a tag sequence at the N- or C-terminus, in particular a polyhistidine tag.

Suitably, the GDS may comprise a C-terminal polyhistidine tag, for example a hexahistidine tag.

Contrary to the teaching of Cascón et al, the present inventors have found that it is possible to obtain small amounts of the compounds of general formula (I) using native germacrene D synthase from *Solidago canadensis* SEQ ID NO: 1; (I. Prosser et al, *Phytochemistry*, 2002, 60, 691-702; C. O. Schmidt et al, *Chirality*, 1999, 11, 353-362; N. Bulow and W. A. Koning, *Phytochemistry*, 2000, 55, 141-168).

However, by using a rational approach to exploiting the chemical biology of (S)-germacrene D synthase (GDS), improved docking of substrates can be achieved by reducing specific aspects of steric hindrance relating to novel substrates. Thus, sequence alignment of GDS with 5-epi-aristolochene synthase and comparison of aromatic residues at or near the active site allowed the inventors to identify residues likely to be in close proximity to the substrate during the catalytic cycle. In particular, Y406 of GDS is a conserved residue corresponding to Y404 in 5-epi-aristolochene synthase and is potentially involved in ensuring the correct ring closure occurs and so is proximal to both ends of the folded up farnesyl chain within the active site. Thus because hydrogen atoms in the 14 and 15 positions of (S)-germacrene D are close to the Y406 of GDS and its dissociated electron orbitals, this tyrosine could be replaced by phenylalanine, sterically smaller but similar in terms of electron density. Indeed this site directed mutant enzyme, (S)-germacrene D synthase, Y406F, was considerably more effective as a synthase particularly for production of the compounds of general formula (I) and the compounds in which R² is H and R² is methyl were produced using this modified enzyme in isolated yields of 45% and 73% respectively.

Therefore, suitably, the GDS enzyme used in the production of the compounds of general formula (I) is modified to have an alternative residue in place of the tyrosine residue at position 406 of the native enzyme. Suitably, the tyrosine residue will be replaced by a smaller residue, for example phenylalanine, leucine, isoleucine, valine or alanine, with phenylalanine being particularly suitable.

The modified GDS polypeptide forms a further aspect of the invention.

In yet further aspects of the invention there are provided:
a nucleic acid sequence encoding the modified GDS polypeptide;
a vector comprising the nucleic acid sequence; and
a cell transfected or transformed with a nucleic acid molecule or vector.

Suitably, the vector is an expression vector adapted to express the nucleic acid molecule according to the invention.

The cell may be a eukaryotic cell or prokaryotic cell. For example the cell may be selected from the group consisting of; a fungal cell, insect cell, a plant cell, bacterial cell.

Suitable bacterial and fungal cells include *E. coli* cells and *S. cerevisiae* cells with *E. coli* cells being particularly suitable.

If microorganisms are used as organisms in the process according to the invention, they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the organisms as described above by processes known to the skilled worker, for example by extraction, distillation, crystallization, if appropriate precipitation with salt, and/or chromatography. To this end, the organisms can advantageously be disrupted beforehand. In this process, the pH value is advantageously kept between pH 4 and 12, preferably between pH 6 and 9, especially preferably between pH 7 and 8.

An overview of known cultivation methods can be found in the textbook by Chmiel (Bioprozeßtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono, di or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid. Nitrogen sources are usually organic or inorganic nitrogen compounds or materials comprising these compounds. Examples of nitrogen sources comprise ammonia in solution or gaseous form or ammonium salts such as ammonium sulfate, ammonium chloride, ammonium phosphate, ammonium carbonate or ammonium nitrate, other nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans (thiols) may be used as sources of sulfur for the production of sulfur-containing fine chemicals, in particular of methionine.

Phosphoric acid, potassium dihydrogenphosphate or dipotassium hydrogenphosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broths obtained in this way, in particular those comprising polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

As discussed above, compounds of general formula (I) have semiochemical properties and act as either insect repellent or insect attractants.

Therefore, in a further aspect of the invention there is provided an insect repellent composition comprising a compound of formula (I) as defined above and a suitable carrier, provided that the compound of general formula (I) is not (S)-14,15-dimethylgermacrene D (i.e. the compound of general formula (I) in which $R^2$ and $R^3$ are methyl and $R^1$, $R^4$ and $R^5$ are H).

The term "carrier" denotes an organic or inorganic ingredient, natural or synthetic, with which the active ingredient is combined to facilitate application. Compositions according to the invention can be solid or fluid, wherein fluid comprises gas and liquid states.

Suitable compounds of general formula (I) for use in the insect repellent compositions are those in which:
each of $R^1$, $R^2$ and $R^4$ is H;
$R^3$ is methyl, ethyl, n-propyl, iso-propyl or cyclopropyl; and
$R^5$ is H, methyl, ethyl, n-propyl, iso-propyl or cyclopropyl.

More suitably in the insect repellant composition, $R^5$ of general formula (I) is H, methyl or ethyl, especially H or methyl and particularly H.

Still more suitable compounds of general formula (I) for use in the insect repellent composition are those in which each of $R^1$, $R^2$, $R^4$ and $R^5$ is H and $R^3$ is methyl or ethyl. Most suitably in the insect repellent composition, the compound of general formula (I) is (S)-15-methylgermacrene D i.e. the compound of general formula (I) in which $R^1$, $R^2$, $R^4$ and $R^5$ is H and $R^3$ is methyl.

The insect repellent composition may contain one or more addition insect repelling compounds, for example allethrins, DEET (N,N-diethyl-m-toluamide), p-menthane-3,8-diol (PMD), picaridin, Bayrepel, KBR 3023, Nepetalactone, Citronella oil, Neem oil, Bog Myrtle, Dimethyl carbate, Tricyclodecenyl allyl ether, IR3535 (3-[N-Butyl-N-acetyl]-aminopropionic acid, ethyl ester) or anthranilate-based insect repellents.

In one embodiment, the insect repellent composition may be suitable for application to human or animals, for example to the skin, and in this case, the carrier will be suitable for pharmaceutical or veterinary application to the skin.

In an alternative embodiment, there is provided an insect attractant composition comprising a compound of formula (I) and a suitable carrier, provided that the compound of formula (I) is not (S)-15-methylgermacrene D (i.e. the compound of general formula (I) in which $R^2$ is hydrogen).

The carrier may be as described above for the insect repellent composition.

Suitable compounds of formula (I) for use in the insect attractant composition are those in which each of $R^2$, $R^3$ and $R^5$ is independently methyl, ethyl, n-propyl, iso-propyl or cyclopropyl and $R^1$ and $R^4$ are both hydrogen.

In more suitable compounds of general formula (I) for use in the insect attractant composition:
each of $R^1$ and $R^4$ is H;
each of $R^2$ and $R^3$ is independently methyl, ethyl, n-propyl, iso-propyl or cyclopropyl; and
$R^5$ is H, methyl, ethyl, n-propyl, iso-propyl or cyclopropyl, but particularly H.

Particularly suitable compounds of general formula (I) for use in the insect attractant composition are those in which:
each of $R^1$, $R^4$ and $R^5$ is H;
each of $R^2$ and $R^3$ is independently methyl or ethyl.

Suitably, in the insect attractant composition the compound of general formula (I) is (S)-14,15-dimethylgermacrene D, i.e. the compound in which each of $R^1$, $R^4$ and $R^5$ is H and each of $R^2$ and $R^3$ is methyl.

In some cases, the insect attractant composition also comprises an insecticide.

Insecticides are substances which are toxic to insects and have a broad application in agricultural, public health, industry, as well as household and commercial uses. Insecticides are typically classified based on their structure and mode of action e.g. many insecticides act upon the nervous system of the insect (e.g., cholinesterase (ChE) inhibition) while others act as growth regulators or endotoxins.

In addition, the insect attractant composition may comprise a controlled release medium selected from the group consisting of rubber, polythene, hollow fibres, plastic sandwiches, plastic membranes and cellulosic materials, so that the attractant is released over a period of days at a concentration effective to attract insects.

The insect attractant composition of the invention may be used in combination with an insect trapping device and therefore in a further aspect of the invention there is provided an insect trapping device comprising the insect attractant composition of the present invention.

The insect attractant composition acts as bait for insects, for example ants, cockroaches, flies, aphids, mosquitoes or moths. In particular, the composition may be an attractant for aphids such as the grain aphid (*Sitobion avenae*).

In some cases, the composition may be a controlled release composition containing a controlled release medium as described above.

The insect trapping device may also comprise an insecticide which may be included in the insect attractant composition or alternatively may be provided as a separate composition.

According to an aspect of the invention there is provided a composition according to the invention for use in the treatment of insect infestations on animals or plants. The composition may be the repellent composition, in which case it may be applied to the animal or plant. Alternatively, it may be the attractant composition, in which case it may be applied to a site adjacent the plants, for example in an insect trapping device.

The animal suffering from insect infestation may be a mammal, which may be either a human or a non-human mammal such as a cat, dog, rodent, cattle, sheep, poultry or pigs.

Plants suffering from insect infestations may be woody plants for example poplar; *eucalyptus*; Douglas fir; pine; walnut; ash; birch; oak; teak; spruce. Alternatively, the plant may be selected from crop plants, for example: corn (*Zea mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*helianthus annuas*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Iopmoea batatus*), cassava (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

More suitably, the compositions of the present invention are used for the protection of crop plants (for example, cereals and pulses, maize, wheat, barley, rye, potatoes, tapioca, rice, sorghum, millet, cassava, barley, pea, oil-seed plants such as cotton, soybean, safflower, sunflower, Brassica, maize, alfalfa, palm, coconut, etc. or leguminous plants and other root, tuber or seed crops. Important seed crops are oil-seed rape, sugar beet, maize, sunflower, soybean, and sorghum. Horticultural plants to which the present invention may be applied may include lettuce, endive, and vegetable brassicas including cabbage, broccoli, and cauliflower, and carnations and geraniums. The present invention may be applied in tobacco, cucurbits, carrot, strawberry, sunflower, tomato, pepper, chrysanthemum. Leguminous plants include beans and peas. Beans include guar, locust bean, fenugreek, soybean, garden beans, cowpea, mungbean, lima bean, fava bean, lentils, chickpea, etc.

According to an aspect of the invention there is provided a method of repelling insects comprising providing an insect repellent composition according to the invention in an area affected by insect infestation.

According to an aspect of the invention there is provided a method of attracting insects comprising providing an insect attractant composition according to the invention in an area affected by insect infestation.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

BRIEF DESCRIPTION OF THE DRAWINGS

The invention will now be described in greater detail with reference to the examples and to the drawings in which.

Figure 1:
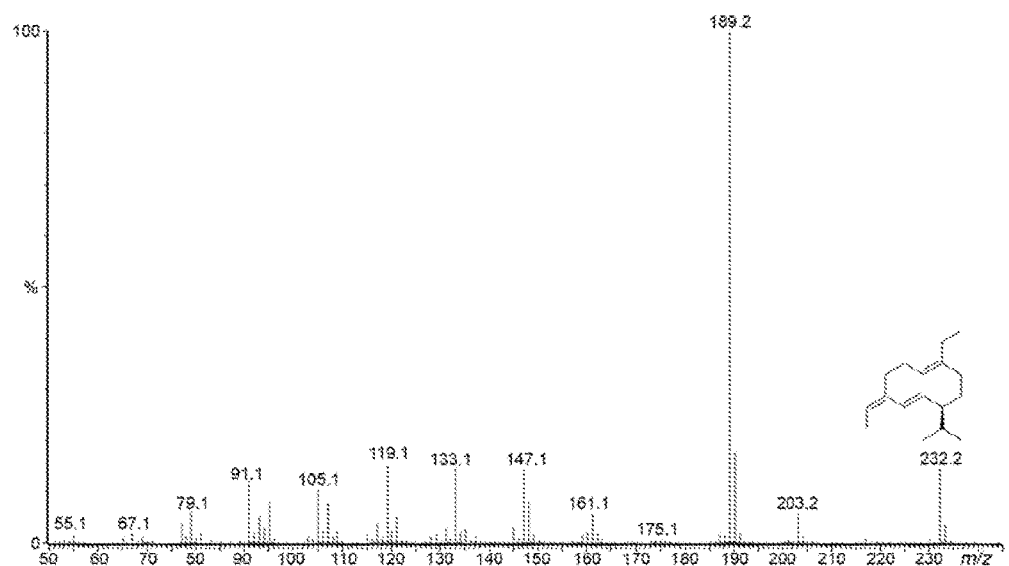
FIG. 1 is a gas chromatogram of the pentane extractable products from incubation of 14,15-dimethylfarnesyl diphosphate (compound of general formula (II) where $R^1$, $R^4$ and $R^5$ are H and $R^2$ and $R^3$ are methyl) with Y406F-GDS-His$_6$. (S)-14,15-dimethylgermacrene D (compound of general formula (I) where $R^1$, $R^4$ and $R^5$ are H and where $R^2$ and $R^3$ are methyl) eluted at 32.83 min.
Figure 2:
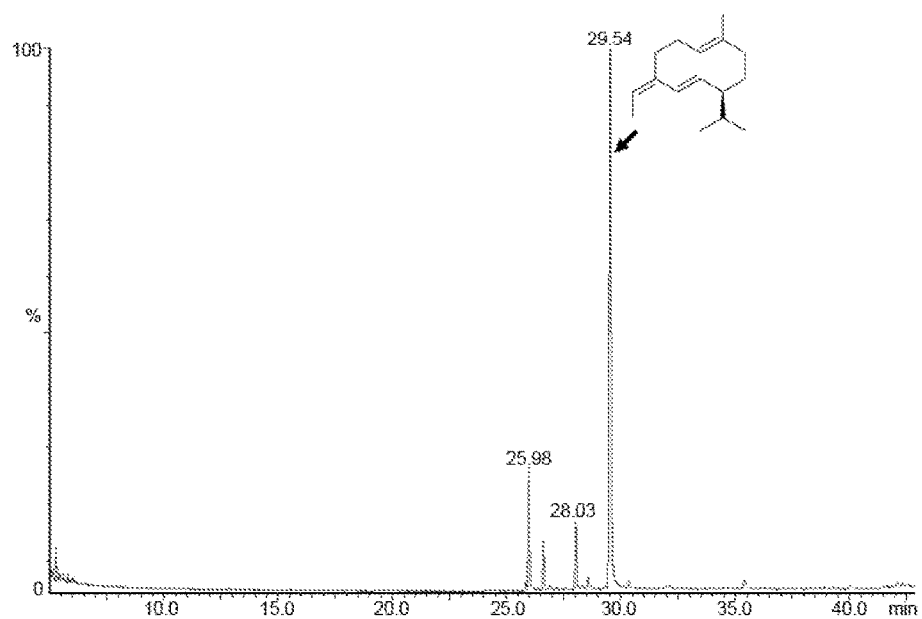
FIG. 2 is a mass spectrum of the product eluting at 32.83 min from incubation of 14,15-dimethylfarnesyl diphosphate with Y406F-GDS-His6.
Figure 3:
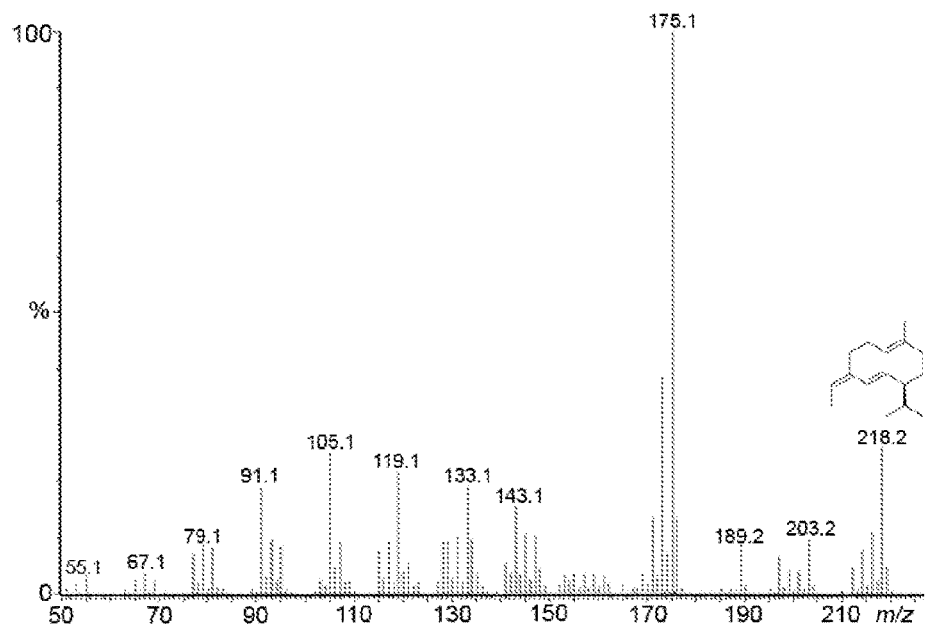
FIG. 3 is a gas chromatogram of the pentane extractable products from incubation of 15-dimethylfarnesyl diphosphate (compound of general formula (II) where $R^1$, $R^2$, $R^4$ and $R^5$ are H and $R^3$ is methyl) with Y406F-GDS-His6. 15-methyl (S)-germacrene D (compound of general formula (I) where $R^1$, $R^2$, $R^4$ and $R^5$ are H and $R^3$ is methyl) eluted at 29.54 min.
Figure 4:
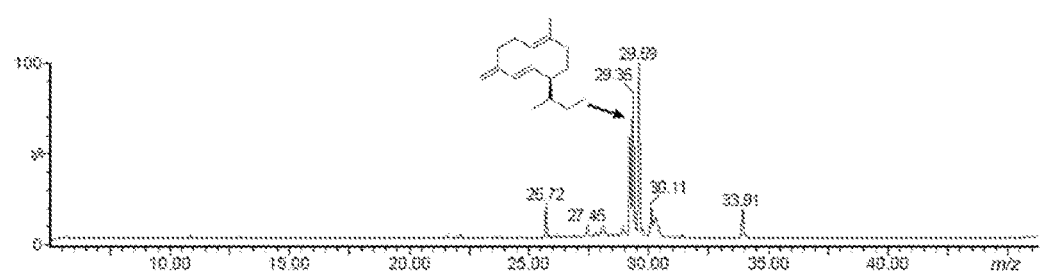
FIG. 4 is a mass spectrum of the product eluting at 29.54 min from incubation of 15-dimethylfarnesyl diphosphate with Y406F-GDS-His6.
Figure 5:
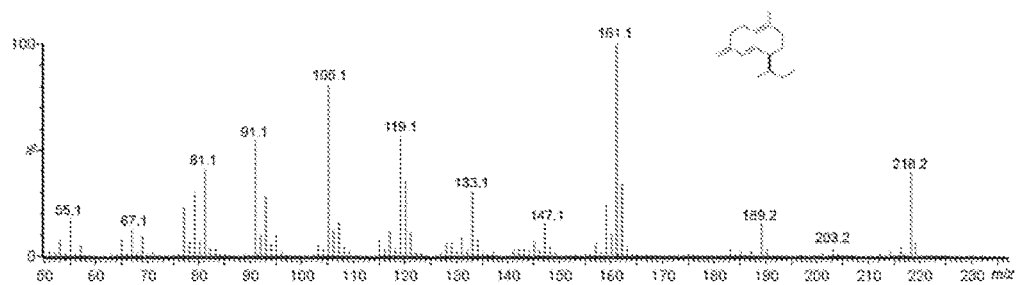
FIG. 5 is a gas chromatogram of the pentane extractable products from the incubation of 12-methylfarnesyl diphosphate (compound similar to general formula (II) in which $R^2$, $R^3$, $R^4$ and $R^5$ are H and $R^1$ is methyl). The germacrene D analogue (compound similar to general formula (I) where $R^2$, $R^3$, $R^4$ and $R^5$ are H and $R^1$ is methyl) eluted at 29.35 minutes.
Figure 6:
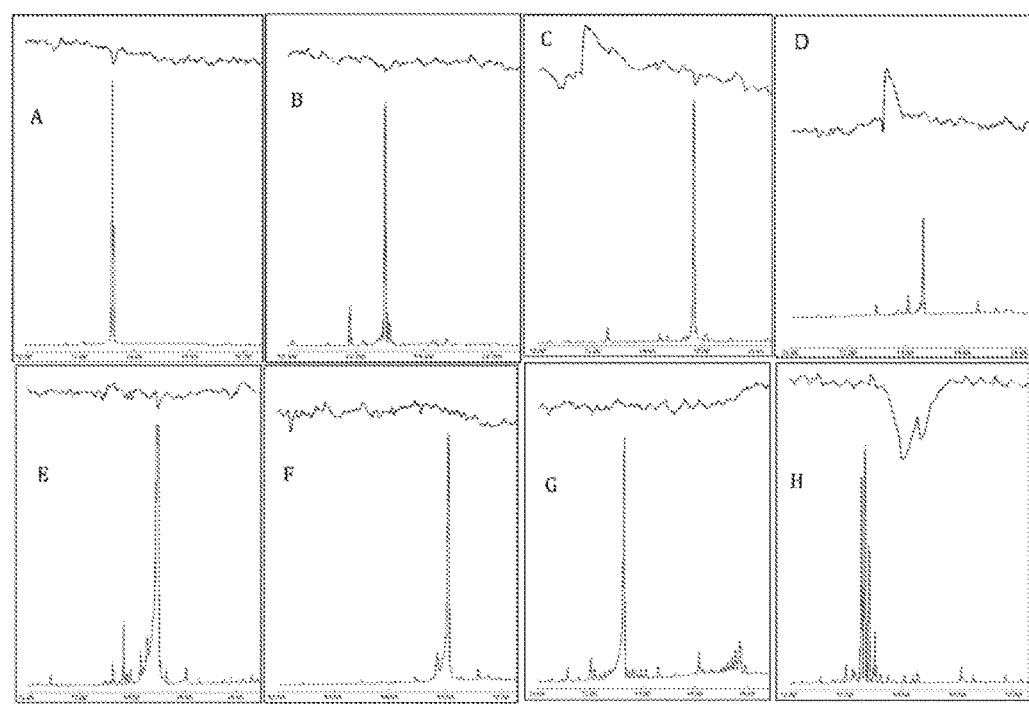
FIG. 6 is a coupled gas chromatography-electroantennography (GC-EAG) with the grain aphid, Sitobion avenae. Upper traces=EAG response, lower traces=GC response.

A—(S)-germacrene D (comparator compound Ia); B—(R)-germacrene D (III); C—(S)-14-methylgermacrene D (; D—(S)-12-methylgermacrene D; E—(S)-15-methylgermacrene D; F—(S)-14,15-dimethylgermacrene D (compound of general formula (I) where $R^2$ and $R^3$ are methyl); G—(S)-1-fluorogermacrene D; H—germacrane (IV).

DETAILED DESCRIPTION

Materials and Methods

All chemicals were purchased from Sigma-Aldrich unless otherwise stated. All were of analytical quality or better and used as received unless otherwise stated.

$^1$H, $^{31}$P and $^{13}$C NMR spectra were measured on a Bruker® Avance III 600 NMR spectrometer, a Bruker® Avance 500 NMR spectrometer or a Bruker® Avance DPX400 NMR spectrometer and are reported as chemical shifts in parts per million downfield from tetramethylsilane, multiplicity (s=singlet, d=doublet, t=triplet, q=quartet, m=multiplet), coupling constant (to the nearest 0.5 Hz) and assignment, respectively. Assignments are made to the limitations of COSY, DEPT 90/135, gradient HSQC and gradient HMBC spectra. CDCl$_3$ was filtered through basic alumina prior to use in NMR spectroscopy. EI$^+$ mass spectra were measured on a Micromass™ LCT Premier™ XE mass spectrometer (VVaters Corporation, Milford, Mass., USA). GCMS was performed on a Hewlett Packard Agilent™ 6890 GC fitted with a J&W Scientific DB-5MS column (30 m×0.25 mm internal diameter) and a Micromass™ GCT Premier™ detecting in the range m/z 50-800 in EI$^+$ mode scanning once a second with a scan time of 0.9 s. Injections were performed in split mode (split ratio 5:1) at 50° C. Chromatograms were begun with an oven temperature of 50° C. (unless otherwise stated) rising at 4° C. min$^{-1}$ for 25 min (up to 150° C.) and then at 20° C. min$^{-1}$ for 5 min (250° C. final temperature).

Protein Preparation and Purification

Recombinant germacrene D synthase and mutants were overproduced in E. coli (DE3)Star as C-terminal His-tagged fusion proteins and purified by Ni$^{2+}$-affinity chromatography as described by Cascón, O. et al. Chemoenzymatic preparation of germacrene analogues. Chem. Commun. 48, 9702-9704 (2012).

Site Directed Mutagenesis of Recombinant GDS

The Quickchange site-directed mutagenesis kit (Stratagene) was used to introduce the desired mutations according to the manufacturer's instructions. The primers used for mutagenesis were as follows:

```
for W275A
                                     (SEQ ID No: 2)
5' CTGGTAGAGCTGTACTTTGCGGTACTGGGCGTTTATTTC 3'
and
                                     (SEQ ID No: 3)
5' GAAATAAACGCCCAGTACCGCAAAGTACAGCTCTACCAG 3';

for W275L
                                     (SEQ ID No: 4)
5' CTGGTAGAGCTGTACTTTCTGGTACTGGGCGTTTATTTC 3'
and
                                     (SEQ ID No: 5)
5' GAAATAAACGCCCAGTACCAGAAAGTACAGCTCTACCAG 3';
```

-continued for W275F (SEQ ID No: 6)
5' GGTAGAGCTGTACTTTTTCGTACTGGGCGTTTATTTC 3'
and (SEQ ID No: 7)
5' GAAATAAACGCCCAGTACGAAAAAGTACAGCTCTACC 3';

for Y524A (SEQ ID No: 8)
5' CGTGATCGACATGCTGGCGAAGAATGACGACAACC 3'
and (SEQ ID No: 9)
5' GGTTGTCGTCATTCTTCGCCAGCATGTCGATCACG 3';

for Y524L (SEQ ID No: 10)
5' GCGTGATCGACATGCTGCTGAAGAATGACGACAACC 3'
and (SEQ ID No: 11)
5' GGTTGTCGTCATTCTTCAGCAGCATGTCGATCACGC 3';

for Y524F (SEQ ID No: 12)
5' GTGATCGACATGCTGTTCAAGAATGACGACAAC 3'
and (SEQ ID No: 13)
5' GTTGTCGTCATTCTTGAACAGCATGTCGATCAC 3';

for Y406S (SEQ ID No: 14)
5' GAATCTGACGGGTGGCAGCAAAATGCTGACGACG 3'
and (SEQ ID No: 15)
5' CGTCGTCAGCATTTTGCTGCCACCCGTCAGATTC 3';

for Y406G (SEQ ID No: 16)
GAATCTGACGGGTGGCGGCAAAATGCTGACGACG 3'
and (SEQ ID No: 17)
5' CGTCGTCAGCATTTTGCCGCCACCCGTCAGATTC 3';

for Y406A (SEQ ID No: 18)
5' GAATCTGACGGGTGGCGCGAAAATGCTGACGACG 3'
and (SEQ ID No: 19)
5' CGTCGTCAGCATTTTCGCGCCACCCGTCAGATTC 3';

for Y406V (SEQ ID No: 20)
5' GAATCTGACGGGTGGCGTGAAAATGCTGACGACG 3'
and (SEQ ID No: 21)
5' CGTCGTCAGCATTTTCACGCCACCCGTCAGATTC 3';

for Y406I (SEQ ID No: 22)
5' GAATCTGACGGGTGGCATTAAAATGCTGACGACG 3'
and (SEQ ID No: 23)
5' CGTCGTCAGCATTTTAATGCCACCCGTCAGATTC 3';

for Y406L (SEQ ID No: 24)
5' GAATCTGACGGGTGGCCTGAAAATGCTGACGACG 3'
and (SEQ ID No: 25)
5' CGTCGTCAGCATTTTCAGGCCACCCGTCAGATTC 3';

for Y406F (SEQ ID No: 26)
5' GAATCTGACGGGTGGCTTTAAAATGCTGACGACG 3'
and (SEQ ID No: 27)
5' CGTCGTCAGCATTTTAAAGCCACCCGTCAGATTC 3';

for Y406W (SEQ ID No: 28)
5' CTGACGGGTGGCTGGAAAATGCTGACGAC 3'
and (SEQ ID No: 29)
5' GTCGTCAGCATTTTCCAGCCACCCGTCAG 3'.

Plasmids were purified from overnight cultures (10 mL LB medium containing ampicillin 50 μmol/mL) using the QIAGEN miniprep kit as described by the manufacturer. Mutations were confirmed by DNA sequence analysis using the internal Walesbiogrid facilities (School of Bioscience, Cardiff University, UK).

Example 1: Synthesis of 14,15-Dimethylfarnesyl Diphoshate (IIg)

The title compound was prepared from β-ketoester V according to the reaction Scheme 1.

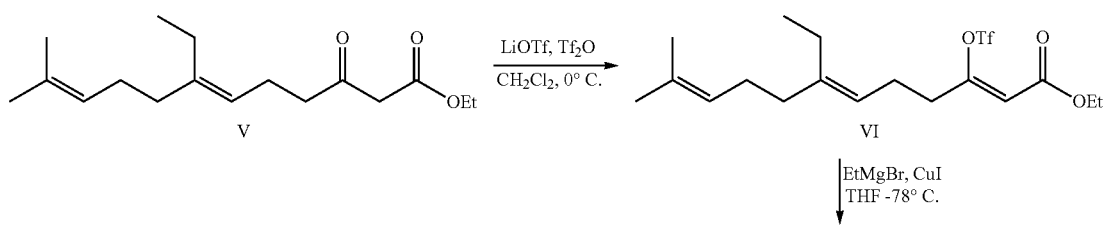

-continued

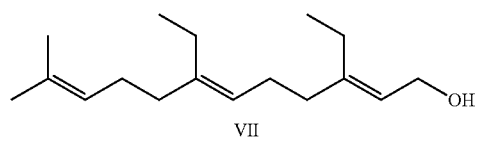

VII

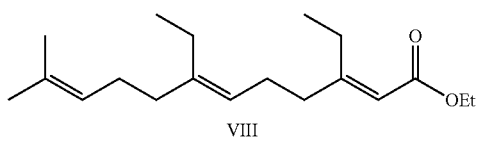

VIII

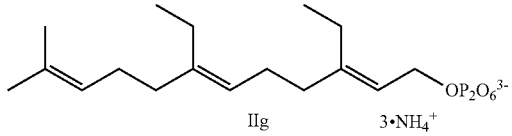

IIg    3•NH$_4^+$

A. Synthesis of (2E,6E) Ethyl 3,7-diethyl-11-methyldodeca-2,6,10-trienoate (VII)

To a stirred solution of V (Cascón et al; ChemPlusChem 78, 1334-1337 (2013)), (0.35 g, 1.50 mmol) and lithium trifluoromethanesulfonate (0.78 g, 5.0 mmol) in dry CH$_2$Cl$_2$ (38 mL) under argon at 0° C. was added triethylamine (0.7 mL, 5.0 mmol) followed by trifluoromethanesulfonic anhydride (0.32 mL, 1.90 mmol). The mixture was stirred at 0° C. for 2 h before quenching with the addition of saturated NH$_4$Cl solution (20 mL). This mixture was diluted with CH$_2$Cl$_2$ (20 mL) and the separated aqueous phase was extracted with CH$_2$Cl$_2$ (2×10 mL). The pooled organic extracts were washed with water (30 mL) and brine (30 mL) before drying (MgSO$_4$), filtration and concentration under reduced pressure. This gave the enol triflate VI as dark oil that was used directly without further purification (0.58 g, 83%).

To a stirred suspension of CuI (0.95 g, 5.00 mmol) in THF (12 mL) at 0° C. was added drop-wise, ethylmagnesium bromide (3.0 M solution in diethyl ether, 3.33 mL, 10.0 mmol). The solution was stirred for 30 minutes, whereupon an opaque black colour formed. The stirred reaction mixture was then cooled to −78° C. and a solution of VI (0.58 g, 1.25 mmol) in anhydrous THF (4 mL) was added via a needle and the reaction was stirred at this temperature for 2.5 h before quenching by addition of saturated aqueous NH$_4$Cl solution (20 mL). Resulting emulsions were dissolved by addition of concentrated aqueous NH$_4$OH solution and stirring overnight. The separated aqueous layer was extracted with ethyl acetate (3×10 mL) and the combined organic extracts were washed with water (2×30 mL) and brine (30 mL) before drying (MgSO$_4$), filtration and concentration under reduced pressure. The residual oil was purified by flash chromatography on silica gel (19:1 hexane; ethyl acetate). The title compound was isolated as colourless oil (185 mg, 52%).

HRMS (m/z ES$^+$): calcd. for C$_{19}$H$_{32}$O$_2$ 292.2402; found 292.2407;

$\delta_H$ (400 MHz, CDCl$_3$) 0.95 (3H, t, J=7.5 Hz, C=CHCH$_2$CH$_3$), 1.07 (3H, t, J=7.5 C=CHCH$_2$CH$_3$), 1.27 (3H, t, J=7.0 Hz, OCH$_2$CH$_3$), 1.59 (3H, s, CH$_3$C=CH), 1.67 (3H, s, CH$_3$C=CH), 1.98-2.05 and 2.03-2.04 (12H, m, 2×CH$_2$CH$_2$ and 2×CH=CCH$_2$CH$_3$), 4.25 (2H, q, J=7.0 Hz, OCH$_2$CH$_3$), 5.01-5.20 (2H, m, 2×C=CH), 5.72 (1H, s, C=CHCO$_2$Et);

$\delta_C$ (62.5 MHz, CDCl$_3$) 12.97, 13.18, 14.29, 17.68 and 23.15 (CH$_3$), 25.34, 25.67, 25.78, 26.84, 36.43, 38.27 and 59.13 (CH$_2$), 114.79, 122.51 and 124.31 (3×C=CH), 131.33 141.91 and 165.53 (3×C=CH), 166.45 (C=O).

B. Synthesis of (2E,6E) 3,7-Diethyl-11-methyldodeca-2,6,10-trienol (VIII)

To a stirred suspension of VII (0.18 mg, 0.60 mmol) in toluene (3.1 mL) at −78° C. was added DIBAL-H (1.5 M in toluene, 1.30 mL, 1.80 mmol), the solution was stirred at this temperature for 2 h. The reaction was quenched by addition of 2 M HCl (10 mL), diluted with CH$_2$Cl$_2$ (10 mL) and stirred for 1 h at room temperature. The aqueous layer was extracted with CH$_2$Cl$_2$ (2×10 mL) and the pooled organic layers were washed with aqueous saturated NaHCO$_3$ solution (3×10 mL), brine (2×15 mL), dried over MgSO$_4$ and then concentrated under reduced pressure. The crude product was purified by flash chromatography on silica gel (eluting with 3:1 hexane-ethyl acetate) to give the title compound as a colourless oil (0.16 mg, 73% yield).

HRMS (m/z APCI [M+H$^+$—H$_2$O]) calcd. for C$_{17}$H$_{29}$ 233.2269; found 233.2275;

$\delta_H$ (400 MHz, CDCl$_3$) 0.94-1.01 (6H, m, 2×CH$_2$CH$_3$), 1.60 (3H, s, CH=CCH$_3$), 1.68 (3H, s, CH=CCH$_3$) 1.97-2.13 (12H, m, 6×CH$_2$), 4.16 (2H, d, J=7.0 Hz, CH$_2$O), 5.09 (2H, m, 2×C=CH), 5.38 (1H, t, J=7.0 Hz, C=CHCH$_2$O).

$\delta_C$ (62.5 MHz, CDCl$_3$) 13.20, 13.65, 17.68 and 23.21 (CH$_3$), 23.54, 25.65, 26.22, 26.96, 36.51 and 36.75 (CH$_2$), 59.09 (CH$_2$OH), 122.89, 123.43 and 124.46 (C=CH), 131.26, 141.25 and 145.69 (C=CH)

C. Synthesis of Trisammonium (2E,6E)-3,7-diethyl-11-methyldodeca-2,6,10-trienyl diphosphate (14,15-Dimethylfarnesyl diphosphate) (IIg)

A stirred suspension of LiCl (0.27 g, 6.4 mmol) in anhydrous DMF (5.3 mL) was cooled to 0° C. (ice bath) and then S-collidine (0.3 mL, 2.4 mmol) and methanesulfonyl chloride (50 μL, 0.64 mmol) were added. The solution was stirred for 15 min during which time a white cloudy precipitate formed. Alcohol VII (100 mg, 0.40 mmol) was added drop-wise as a solution in anhydrous DMF (1 mL) and the reaction was stirred at 0° C. for 3 h. The mixture was diluted with cold pentane (4 mL) then poured onto ice (25 g) and the resulting aqueous layer was extracted with pentane (3×10 mL). The pooled organic layers were washed with saturated CuSO₄ solution (3×10 mL), saturated NaHSO₄ solution (2×10 mL) and brine (2×10 mL) before drying (MgSO₄) and filtration. The solution was concentrated under reduced pressure and the resulting crude allylic chloride was used directly without further purification.

To a solution of the crude allylic chloride in anhydrous CH₃CN (1 mL) was added tris-(tetrabutylammonium) hydrogendiphosphate (0.7 g, 1.8 mmol) and the mixture was stirred at room temperature for 15 h. The solvent was removed under reduced pressure and the residue was dissolved in ion-exchange buffer (25 mM NH₄HCO₃ containing 2% i-PrOH, 1 mL). This solution was slowly passed through a column containing 30 equiv. of DOWEX 50W-X8 (100-200 mesh) cation exchange resin (NH₄⁺ form) that had been pre-equilibrated with two column volumes of ion-exchange buffer. The column was eluted with two column volumes of ion-exchange buffer at a flow rate of one column volume per 15 min. Once ion exchange was complete, fractions containing product (as judged by TLC in 6:3:1 i-PrOH:c.NH₃:H₂O, staining with Hanessian's stain) was lyophilized to dryness. The white solid was triturated with MeOH (3×10 mL) and the organic extracts were concentrated to dryness affording a yellow solid that was cleaned with Et₂O (3×3 mL) to give the title compound as a white solid (64 mg, 36%). The residue from the trituration was further purified by reverse-phase HPLC (150×21.2 mm Phenomenex Luna™ column, eluting with 10% B for 20 min, then a linear gradient to 60% B over 25 min and finally a linear gradient to 100% B over 5 min.; solvent A: 25 mM NH₄HCO₃ in water, solvent B: CH₃CN, flow rate 5.0 mL/min, detecting at 220 nm, retention time 39.3 min). Once purification was complete the solution was again lyophilized to dryness giving a further batch of the title compound as a fluffy white solid (34 mg, 18.9% yield).

HRMS (m/z ES⁻) calcd. for $C_{17}H_{31}O_7P_2$ 409.2545; found 409.2539;

$\delta_H$ (400 MHz, D₂O) 0.8-0.91 (6H, m, 2×CH₂CH₃), 1.50 (3H, s, C=CCH₃), 1.56 (3H, s, C=CCH₃) 1.92-2.03 (12H, m, 6×CH₂), 4.37 (2H, m, CH₂O), 5.07 (2H, t, J=6.0 Hz, 2×C=CH), 5.32 (1H, t, J=6.5 Hz, C=CHCH₂O);

$\delta_P$ (202.5 MHz, ²H₂O) −10.41 (d, $J_{PP}$=22.5 Hz), −8.30 (d, $J_{PP}$=22.5 Hz).

Other compounds of general formula (II) can be synthesised by an analogous method starting from an alternative β-ketoester.

Example 2: Preparation of (S)-germacrene D Analogues

Germacrene analogues were produced from the appropriate farnesyl diphosphate according to Scheme 2 by enzymatic coversion using GDP or a modified GDP.

Scheme 2

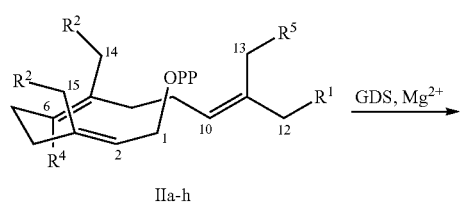

IIa-h

-continued

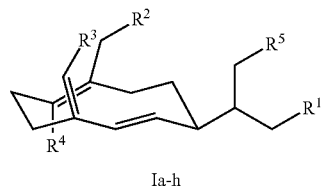

Ia-h

| Substrate | Product |
|---|---|
| IIa | Comparator Compound Ia (S)-germacrene D |
| IIb | Comparator Compound Ib (S)-12-methylgermacrene D |
| IIc | Comparator Compound Ic (S)-14-methylgermacrene D |
| IId | Comparator Compound Id (S)-14-fluorogermacrene D |
| IIe | Comparator Compound Ie (S)-15-fluorogermacrene D |
| IIf | Compound If (S)-15-methylgermacrene D |
| IIg | Compound Ig (S)-14,15-dimethylgermacrene D |
| IIh | Comparator Compound Ih (S)-1-fluorogermacrene D |

Incubations of FDP analogues with GDS-His₆ and Y406F GDS-His₆ were optimised to generate maximum conversions as previously described (Cascón et al, in *Chem. Commun.*, 48, 9702-9704 (2012) and Cascón et al; *ChemPlusChem* 78, 1334-1337 (2013)).

Results of Enzyme Kinetics Experiments

The kinetics parameters for the conversion of farnesyl diphosphate and analogues thereof to (S)-germacrene D and analogues thereof using different variant GDS enzymes are shown in Tables 1 to 3.

TABLE 1

Kinetic parameters of Y524F and W275F mutants

| | $K_M$ (μM) | | $k_{cat}$ (s⁻¹) | | $k_{cat}/K_M$ 10³ (M⁻¹·s⁻¹) | |
|---|---|---|---|---|---|---|
| GDS | value | error | value | error | value | error |
| WT | 3.60 | 0.26 | 0.0094 | 0.0002 | 2.612 | 0.191 |
| Y524F | 5.34 | 0.43 | 0.0143 | 0.0004 | 2.669 | 0.227 |
| W275F | 2.06 | 0.21 | 0.0082 | 0.0002 | 3.971 | 0.405 |

TABLE 2

Kinetics parameters of Y406 mutants

| | $K_M$ (μM) | | $k_{cat}$ (s⁻¹) | | $k_{cat}/K_M$ 10³ (M⁻¹·s⁻¹) | |
|---|---|---|---|---|---|---|
| GDS | value | error | value | error | value | error |
| WT (GDS-His₆) | 3.60 | 0.26 | 0.0094 | 0.0002 | 2.612 | 0.191 |
| Y406W | 3.14 | 0.26 | 0.0005 | 0.00001 | 0.139 | 0.012 |
| Y406F | 12.75 | 0.81 | 0.0853 | 0.0003 | 6.692 | 0.426 |
| Y406L | 8.13 | 0.53 | 0.0543 | 0.0012 | 6.679 | 0.459 |
| Y406I | 4.37 | 0.44 | 0.0319 | 0.0010 | 7.299 | 0.782 |
| Y406V | 4.17 | 0.57 | 0.0131 | 0.0003 | 4.363 | 0.394 |
| Y406A | 1.46 | 0.09 | 0.0132 | 0.0002 | 9.043 | 0.562 |
| Y406S | — | — | — | — | — | — |
| Y406G | — | — | — | — | — | — |

TABLE 3

Turnover kinetics of IIa, IIg and IIf with GDS-His$_6$ and Y406F-GDS.

| | GDS-His$_6$ | | | Y406F-GDS-His$_6$ | | |
|---|---|---|---|---|---|---|
| | $K_M$ mM | $k_{cat}$ s$^{-1}$ | $k_{cat}/K_M$ M$^{-1}$ s$^{-1}$ | $K_M$ mM | $k_{cat}$ s$^{-1}$ | $k_{cat}/K_M$ M$^{-1}$ s$^{-1}$ |
| IIa | 3.60 ± 0.26 | 0.0094 ± 0.0002 | 2600 ± 200 | 12.75 ± 0.81 | 0.0853 ± 0.0003 | 6700 ± 400 |
| IIg | 2.63 ± 0.39 | 0.0043 ± 0.0004 | 1600 ± 300 | 12.39 ± 3.85 | 0.0228 ± 0.0028 | 1800 ± 600 |
| IIf | 5.02 ± 1.62 | 0.0068 ± 0.0008 | 1400 ± 500 | 5.82 ± 1.20 | 0.0222 ± 0.0011 | 3800 ± 800 |

For both compounds (If) and (Ig), the conversion was most suitably effected using a modified GDS-Y406F enzyme. However, for native (S)-Germacrene D and the other analogues, the native GDS enzyme was used rather than a modified enzyme.

A. Preparation of (S)-14,15-Dimethylgermacrene D (Compound Ig)

For production of (S)-14,15-dimethylgermacrene D 14,15-dimethyl-FDP (IIg) (19 mg, 0.40 mM final concentration) and Y406F-GDS-His$_6$ (12 µM final concentration) were mixed in incubation buffer (20 mM Tris, 5 mM βME, and 10 mM MgCl$_2$, pH 7.5, 10% glycerol for GDS, 50 mL final volume) overlaid with pentane (10 mL). The mixture was gently agitated for 5 days at room temperature and then the separated aqueous layer was thoroughly extracted with further portions of pentane until no product could be detected by GCMS. The pooled pentane extracts were concentrated to dryness and the residue was purified by preparative thin layer chromatography on silica gel impregnated with 1% AgNO$_3$, eluting with 5% acetone in pentane. The title compound was isolated as a colourless oil (14 mg, 73%).

HRMS (m/z, EI$^+$) calcd. for C$_{17}$H$_{28}$ 232.2191; found 232.2191;

$\delta_H$ (600 MHz, CDCl$_3$) 0.79 (3H, d, J=7.0 Hz, (CH$_3$)$_2$CH), 0.85 (3H, d, J=7.0 Hz, (CH$_3$)$_2$CH), 0.86-0.90 (2H, m, (CH$_3$)$_2$CHCHCH$_2$), 0.94 (3H, t, J=7.5 Hz, CH$_3$CH$_2$), 1.37-1.42 (1H, m, (CH$_3$)$_2$CH), 1.68 (3H, d, J=6.0 Hz, CH$_3$CH=C), 1.70-1.75 (2H, m, CH$_2$CEt), 1.85-1.90 (1H, m, 1×CH$_2$CH=CEt), 1.97-2.02 (1H, m, 1×CH$_2$CH=CEt), 2.02-2.09 (1H, m, (CH$_3$)$_2$CHCH), 2.14-2.20 (1H, m, 1×CH$_3$CH=CCH$_2$), 2.25-2.32 (2H, m, CH$_3$CH$_2$), 2.36-2.43 (1H, m, 1×CH$_2$C=CEt), 2.44-2.52 (1H, m, 1×CH$_3$CH=CCH$_2$), 5.03 (1H, dd, J=6 and 11 Hz, CH$_3$CH$_2$C=CH), 5.08 (1H, dd, J=10 and 16 Hz, CH$_3$CH=CCH=CH), 5.38 (1H, q, J=6.0 Hz, CH$_3$CH=C), 5.72 (1H, d, J=6.0 Hz, CH$_3$CH=CCH=CH);

$\delta_C$ (150 MHz, CDCl$_3$) 12.66 (CH$_3$CH$_2$), 13.18 (CH$_3$CH=C), 14.13 (1×(CH$_3$)$_2$CH), 19.28 (1×(CH$_3$)$_2$CH) 20.75 ((CH$_3$)$_2$CHCHCH$_2$) 21.30 (CH$_3$CH$_2$), 22.70 (CH$_2$CEt), 27.09 (CH$_2$CH=CEt), 32.83 ((CH$_3$)$_2$CH), 36.96 (CH$_3$CH=CCH$_2$), 52.57 ((CH$_3$)$_2$CHCH), 120.0 (CH$_3$CH=C), 130.1 (CH=CEt), 133.6 (CH=CHCH (CH$_3$)$_2$), 136.1 (CH=CHCH(CH$_3$)$_2$), 139.4 (CH=CEt), 140.2 (CH$_3$CH=C);

m/z (EI$^+$), 232.2 (22%, M$^+$), 203.2 (8, [M-Et]$^+$), 189.2 (100, [M-(CH$_3$)$_2$CH]$^+$), 175.2 (2), 161.1 (11), 147.1 (30), 133.1 (31), 119.1 (33), 105.1 (25), 91.1 (29), 79.1 (18), 67.1 (7), 55.1 (4).

B. Preparation of (S)-15-methylgermacrene D (If)

The title compound was produced in similar fashion to Compound (Ig). 15-methyl-FDP (IIf) (19 mg, 0.40 mM final concentration) and Y406F-GDS-His$_6$ (12 µM final concentration) were mixed in incubation buffer (20 mM Tris, 5 mM βME, and 10 mM MgCl$_2$, pH 7.5, 10% glycerol for GDS, 200 mL final volume) overlaid with pentane (10 mL). The mixture was gently agitated for 5 days at room temperature and then the separated aqueous layer was thoroughly extracted with further portions of pentane until no product could be detected by GCMS. The pooled pentane extracts were concentrated to dryness and the residue was purified by preparative thin layer chromatography on silica gel impregnated with 1% AgNO$_3$, eluting with 5% acetone in pentane. The title compound was isolated as a colourless oil (8 mg, 45%). HRMS (m/z, EI$^+$) calcd. for C$_{17}$H$_{28}$ 232.2191; found 232.2191;

$\delta_H$ (600 MHz, CDCl$_3$) 0.72-0.80 (3H, m, (CH$_3$)$_2$CHCHCH$_2$), 0.83 (3H, d, J=7.0 Hz, (CH$_3$)$_2$CH), 0.90 (3H, d, J=7.0 Hz, (CH$_3$)$_2$CH), 1.56 (3H, s, CH$_3$C=CH), 1.71 (3H, d, J=7.0 Hz, CH$_3$CH=C), 1.95-2.05, 2.16-2.18, 2.21-2.25, 2.30-2.37 and 2.52-2.54 (7H, m, allylic CHs), 5.14-5.18 (2H, m, CH$_3$CH=CCH=CH and CH$_3$C=CH), 5.42 (1H, q, J=7.0 Hz, CH$_3$CH=C), 5.76 (1H, d, J=6.0 Hz, CH$_3$CH=CCH=CH);

m/z (EI$^+$), 218.2 (28%, M$^+$), 203.2 (10, [M-CH$_3$]$^+$), 189.2 (9), 175.1 (100), 143.1 (18), 133.1 (20), 119.1 (22), 105.1 (25), 91.1 (20), 79.1 (10), 67.1 (4), 55.1 (3).

Example 3

Electrophysiology

Electroantennogram (EAG) recordings were made using Ag—AgCl glass electrodes filled with saline solution [composition as in Maddrell et al, *J. Exp. Biol.* 51, 71 (1969) but without glucose]. The head of an alate virginoparous grain aphid, *Sitobion avenae*, was excised and placed within the indifferent electrode and the tips of both antennae were removed before they were inserted into the recording electrode. The signals were passed through a high impedance amplifier (UN-06, Syntech, Hilversum, the Netherlands) and analysed using a customized software package (Syntech).

The coupled gas chromatography-electrophysiology system (GC-EAG), in which the effluent from the GC column is simultaneously directed to the antennal preparation and the GC detector, has been described previously (Wadhams, The use of Coupled Gas Chromatography Electrophysiological Techniques in the Identification of Insect Pheromones.

*Chromatographic Society Symposium*, Reading, England, UK, Mar. 21-23, 1989, XIV+376P, Plenum Press: New York, U.S.A., pp. 289-298 (1990)). Separation of the required germacrene D analogue and any contaminants present in the sample was achieved on an Agilent® 6890 GC equipped with a cool on-column inlet and an FID, using an HP-1 (50 m×0.32 mm, O.D.×0.52 µm, phase thickness) column with helium as carrier gas (flow rate of 2.5 ml/min).

The oven temperature was maintained at 30° C. for 2 minutes and then ramped at 15°/minute to 250° C.

The outputs from the EAG amplifier and the FID were monitored simultaneously and analysed using the Syntech software package. Peaks eluting from the GC column were judged to be active if they elicited EAG activity in three or more coupled runs.

Behavioural Assay

The responses of individual grain aphids, Sitobion avenae, to test compounds were observed using a Perspex four-arm olfactometer (Pettersson, J.; Ent. Scand. 1, 63-73 (1970); Webster, B., et al. Animal Behav. 79, 451-457 (2010)), which was maintained at 23° C. and lit from above. A filter paper disc was laid in the bottom section of the olfactometer to provide traction for the aphid and the middle and top sections were fitted into place very tightly to give a good seal. The four arms, consisting of the barrels of disposable 10 mL syringes (Plastipak), were fitted tightly into the holes of the middle section, and filtered air was drawn through them and into the body of the olfactometer through a tube inserted into a hole in the centre of the top section and attached to a pump. The measured total flow rate was 200 mL/min and it was assumed that the flow rate through each arm was 50 mL/min. The three control arms each contained a filter paper strip to which had been applied 10□L hexane which had been allowed to evaporate for 30 s. The treatment arm contained a filter paper strip to which the test compound in 10 µL of hexane (20-200 ng µL$^{-1}$) had been applied and left for 30 s for the hexane to evaporate. A single aphid was introduced through the central hole and the suction tube quickly reinserted. The time spent in each arm and in the central zone were recorded, using specialist software (OLFA, Udine, Italy), for the next 16 minutes. The olfactometer was rotated through 90° every 2 min to eliminate any directional bias. Each assay comprised 10 replicates and the mean time spent in treated and control arms were compared using a paired t-test (Genstat).

Results are shown below in Table 5 for compounds and comparator compounds of formula (I) together with (R)-germacrene D (III) and germacrane (IV).

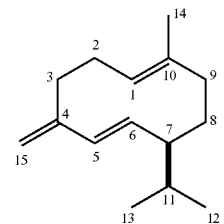

I

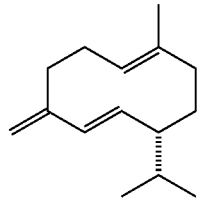

III

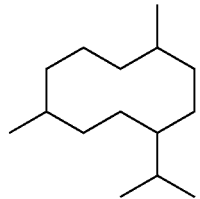

IV

TABLE 5

Behavioural response of cereal aphids, Sitobion avenae, to germacrene D analogues using 4-way olfactometer

| Compound | Dose (µg) | Time (min.) spent in:- Control arms (mean of 3) | Treatment arm | Significance (p) |
| --- | --- | --- | --- | --- |
| (S)-(−)-germacrene D (Ia)* | 0.2 | 2.31 (0.26) | 1.14 (0.25) | 0.005 |
|  | 1.0 | 2.67 (0.190) | 1.63 (0.35) | 0.007 |
|  | 2.0 | 2.29 (0.41) | 0.50 (0.14) | 0.012 |
| (S)-1-fluorogermacrene D (Ih)* | 1.0 | 2.54 (0.27) | 2.62 (0.50) | 0.447 |
|  | 2.0 | 2.60 (0.26) | 2.46 (0.39) | 0.402 |
| (S)-12-methylgermacrene D (Ib)* | 0.9 | 2.21 (0.42) | 1.20 (0.24) | 0.039 |
|  | 1.2 | 2.66 (0.17) | 2.13 (0.25) | 0.075 |
| (S)-14-methylgermacrene D (Ic)* | 0.2 | 2.21 (0.27) | 2.41 (0.73) | 0.409 |
|  | 1.0 | 2.61 (0.28) | 3.27 (0.68) | 0.225 |
|  | 2.0 | 2.01 (0.23) | 1.65 (0.39) | 0.209 |
| (S)-15-methylgermacrene D (If)* | 0.8 | 2.61 (0.26) | 1.38 (0.38) | 0.008 |
|  | 1.0 | 2.52 (0.23) | 1.92 (0.31) | 0.094 |
| (S)-14,15-dimethylgermacrene D (Ig)* | 0.8 | 2.60 (0.22) | 3.38 (0.38) | 0.069 |
|  | 1.0 | 2.27 (0.11) | 2.77 (0.31) | 0.052 |
|  | 1.0 | 2.39 (0.20) | 2.97 (0.40) | 0.032 |
|  | 1.2 | 1.96 (0.21) | 2.92 (0.23) | 0.001 |
| (R)-(+)-germacrene D (III) | 1.0 | 2.57 (0.19) | 3.15 (0.53) | 0.447 |
|  | 2.0 | 1.86 (0.29) | 2.65 (0.52) | 0.108 |
| germacrane (IV) | 1.0 | 2.45 (0.30) | 2.04 (0.58) | 0.265 |
|  | 2.0 | 2.39 (0.24) | 2.38 (0.50) | 0.485 |

*Analogue prepared from FDP using GDS.

Data were recorded as mean (±SE) time spent in control (solvent only) or treatment arms and were analysed using Students T-test.

Example 4: GC-MS Analysis

Gas chromatograms for the products isolated from turnover of 14-methylfarnesyl diphosphate, 14-fluorofarnesyl diphosphate, 15-fluorofarnesyl diphosphate and 6-fluorofarnesyl diphosphate were as previously published (Cascón et al, *Chem. Commun.*, 48, 9702-9704 (2012)).

The invention claimed is:

1. A (S)-germacrene D analogue of general formula (I):

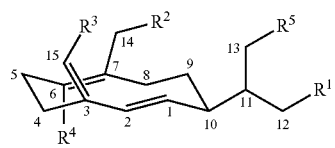

(I)

wherein
R$^1$ is H, methyl, ethyl, n-propyl, iso-propyl or cyclopropyl;
R$^2$ is methyl;
R$^3$ is methyl;
R$^4$ is H, methyl, ethyl, n-propyl, iso-propyl or cyclopropyl;
R$^5$ is H, methyl, ethyl, n-propyl, iso-propyl or cyclopropyl.

2. The compound according to claim 1 wherein, independently or in any combination:
R$^1$ is H, methyl or ethyl;
R$^4$ is H, methyl or ethyl;
R$^5$ is H, methyl or ethyl.

3. The compound according to claim 1 wherein each of R$^1$ and R$^4$ is H.

4. The compound according to claim 1 which is ((S)-14,15-dimethylgermacrene D.

5. The compound according to claim 1 wherein, independently or in any combination:
R$^1$ is H or methyl;
R$^4$ is H or methyl;
R$^5$ is H or methyl.

6. A modified GDS polypeptide comprising a native germacrene D synthase from *Solidago canadensis* SEQ ID NO: 1, which has one or more of the modifications:
tyrosine residue at position 406 replaced by phenylalanine, leucine, isoleucine, valine or alanine;
tryptophan residue at position 275 replaced by phenylalanine;
tyrosine residue at position 524 replaced by phenylalanine.

7. The modified GDS polypeptide according to claim 6 wherein the GDS has one or more of tyrosine at position 406, tryptophan at position 275, and tyrosine at position 524 replaced by phenylalanine.

8. A nucleic acid sequence encoding the modified GDS polypeptide according to claim 6.

9. A vector comprising the nucleic acid sequence according to claim 8.

10. A cell transfected or transformed with the vector according to claim 9.

11. A cell transfected or transformed with the nucleic acid molecule according to claim 8.

12. The process for the preparation of a compound according to claim 1, the process comprising incubating germacrene D synthase (GDS) with a farnesyl diphosphate analogue of general formula (II) or a salt thereof:

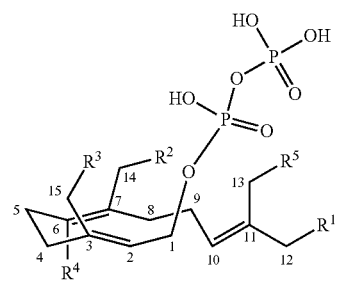

(II)

wherein R$^1$, R$^2$, R$^3$, R$^4$ and R$^5$ are as defined in general formula (I).

13. The process according to claim 12 wherein the germacrene D synthase is a recombinant (S)-germacrene D synthase polypeptide.

14. The process according to claim 13 wherein the recombinant GDS comprises a tag sequence at the N- or C-terminus.

15. The process according to claim 14 wherein the GDS comprises a C-terminal polyhistidine tag.

16. The process according to claim 15 wherein the GDS comprises a C-terminal hexahistidine tag.

17. The process according to claim 14 wherein the recombinant GDS comprises a polyhistidine tag sequence at the N- or C-terminus.

18. The process according to claim 12 wherein the GDS is native germacrene D synthase from *Solidago canadensis* SEQ ID NO: 1.

19. The process according to claim 12 wherein the GDS is native germacrene D synthase from *Solidago canadensis* SEQ ID NO: 1, which has one or more of the modifications:
tyrosine residue at position 406 replaced by phenylalanine, leucine, isoleucine, valine or alanine;
tryptophan residue at position 275 replaced by phenylalanine;
tyrosine residue at position 524 replaced by phenylalanine.

20. The process according to claim 19 wherein the GDS has one or more of tyrosine at position 406, tryptophan at position 275 tyrosine at position 524 replaced by phenylalanine.

21. An insect attractant composition comprising a compound according to claim 1 and a suitable carrier.

22. The insect attractant composition according to claim 21 wherein the compound of general formula (I) is (S)-14,15-dimethylgermacrene D.

23. The insect attractant composition according to claim 21 further comprising an insecticide.

24. The insect attractant composition according to claim 21 further comprising a controlled release medium selected from the group consisting of rubber, polythene, hollow fibres, plastic sandwiches, plastic membranes and cellulosic materials, so that the attractant is released over a period of days at a concentration effective to attract insects.

25. An insect trapping device comprising an insect attractant composition according to claim 21.

26. A method of attracting insects comprising providing an insect attractant composition according to claim 21 in an area affected by insect infestation.

\* \* \* \* \*

SEQUENCE LISTING

<160> NUMBER OF SEQ ID NOS: 29

<210> SEQ ID NO 1
<211> LENGTH: 550
<212> TYPE: PRT
<213> ORGANISM: Solidago canadensis

<400> SEQUENCE: 1

```
Met Ala Ala Lys Gln Gly Glu Val Val Arg Pro Asp Ala Asp Tyr Ser
1               5                   10                  15

Tyr His Pro Ser Leu Trp Gly Asp Gln Phe Leu His Tyr Asp Glu Gln
            20                  25                  30

Glu Asp Asp Gln Val Glu Val Asp Gln Gln Ile Glu Ile Leu Lys Glu
        35                  40                  45

Glu Thr Arg Arg Glu Ile Leu Ser Ser Leu Asp Asp Pro Ala Lys His
    50                  55                  60

Thr Asn Leu Leu Lys Leu Ile Asp Val Ile Gln Arg Leu Gly Ile Ala
65                  70                  75                  80

Tyr Tyr Phe Glu His Glu Ile Thr Gln Ala Leu Asp His Ile Tyr Asn
                85                  90                  95

Val Tyr Gly Asp Glu Trp Asn Gly Gly Ser Thr Ser Leu Trp Phe Arg
            100                 105                 110

Leu Leu Arg Gln Gln Gly Phe Tyr Val Ser Cys Asp Ile Phe Asn Ile
        115                 120                 125

Tyr Lys Leu Asp Asn Gly Ser Phe Lys Asp Ser Leu Thr Lys Asp Ile
    130                 135                 140

Glu Cys Met Leu Glu Leu Tyr Glu Ala Ala Tyr Met Arg Val Gln Gly
145                 150                 155                 160

Glu Ile Ile Leu Asp Glu Ala Leu Glu Phe Thr Lys Thr His Leu Glu
                165                 170                 175

Gln Ile Ala Lys Asp Pro Leu Arg Cys Asn Asn Thr Leu Ser Arg His
            180                 185                 190

Ile Tyr Glu Ala Leu Lys Arg Pro Ile Arg Lys Arg Leu Pro Arg Val
        195                 200                 205

Asp Ala Leu Gln Tyr Met Pro Phe Tyr Glu Gln Gln Asp Ser His Asn
    210                 215                 220

Lys Ser Leu Leu Arg Leu Ala Lys Leu Gly Phe Asn Arg Leu Gln Ser
225                 230                 235                 240

Leu His Lys Lys Glu Leu Ser Gln Leu Ser Lys Trp Trp Lys Glu Phe
                245                 250                 255

Asp Ala Pro Lys Asn Leu Arg Tyr Val Arg Asp Arg Leu Val Glu Leu
            260                 265                 270

Tyr Phe Trp Val Leu Gly Val Tyr Phe Glu Pro Gln Tyr Ser Arg Ser
        275                 280                 285
```

```
Arg Ile Phe Leu Thr Lys Val Ile Lys Met Ala Thr Ile Leu Asp Asp
            290                 295                 300

Thr Tyr Asp Ile His Gly Thr Tyr Glu Glu Leu Glu Ile Phe Thr Lys
305                 310                 315                 320

Ala Val Gln Arg Trp Ser Ile Thr Cys Met Asp Thr Leu Pro Asp Tyr
                325                 330                 335

Met Lys Met Ile Tyr Lys Ser Leu Leu Asp Val Tyr Glu Glu Met Glu
                340                 345                 350

Glu Ile Ile Glu Lys Asp Gly Lys Ala Tyr Gln Val His Tyr Ala Lys
            355                 360                 365

Asp Ser Met Ile Asp Leu Val Thr Ser Tyr Met Thr Glu Ala Lys Trp
370                 375                 380

Leu His Glu Gly His Val Pro Thr Phe Glu Gly Tyr Asn Ser Ile Thr
385                 390                 395                 400

Asn Leu Thr Gly Gly Tyr Lys Met Leu Thr Thr Ser Ser Phe Val Asp
                405                 410                 415

Met Pro Gly Asp Ile Val Thr Gln Glu Ser Phe Arg Trp Ala Leu Asn
                420                 425                 430

Asn Pro Pro Leu Ile Lys Ala Ser Ala Asp Val Ser Arg Ile Met Asp
            435                 440                 445

Asp Ile Val Gly His Lys Glu Glu Gln Arg Lys His Leu Pro Ser
450                 455                 460

Arg Val Glu Met Tyr Met Lys Lys Tyr His Leu Ala Glu Glu Asp Val
465                 470                 475                 480

Tyr Asp Leu Leu Lys Gln Arg Val Glu Asp Ala Trp Lys Asp Leu Asn
                485                 490                 495

Arg Glu Thr Leu Thr Cys Lys Asp Ile His Met Ala Leu Lys Met Arg
                500                 505                 510

Pro Ile Asn Leu Ala Arg Val Ile Asp Met Leu Tyr Lys Asn Asp Asp
            515                 520                 525

Asn Leu Lys Asn Val Gly Gln Glu Ile Gln Asp Tyr Ile Lys Ser Cys
            530                 535                 540

Phe Ile Asn Ala Ile Ser
545                 550

<210> SEQ ID NO 2
<211> LENGTH: 39
<212> TYPE: DNA
<213> ORGANISM: Solidago canadensis

<400> SEQUENCE: 2
ctggtagagc tgtactttgc ggtactgggc gtttatttc                    39

<210> SEQ ID NO 3
<211> LENGTH: 39
<212> TYPE: DNA
<213> ORGANISM: Solidago canadensis

<400> SEQUENCE: 3
gaaataaacg cccagtaccg caaagtacag ctctaccag                    39

<210> SEQ ID NO 4
<211> LENGTH: 39
<212> TYPE: DNA
<213> ORGANISM: Solidago canadensis

<400> SEQUENCE: 4
```

```
ctggtagagc tgtactttct ggtactgggc gtttatttc                                    39

<210> SEQ ID NO 5
<211> LENGTH: 39
<212> TYPE: DNA
<213> ORGANISM: Solidago canadensis

<400> SEQUENCE: 5
gaaataaacg cccagtacca gaaagtacag ctctaccag                                    39

<210> SEQ ID NO 6
<211> LENGTH: 37
<212> TYPE: DNA
<213> ORGANISM: Solidago canadensis

<400> SEQUENCE: 6
ggtagagctg tactttttcg tactgggcgt ttatttc                                      37

<210> SEQ ID NO 7
<211> LENGTH: 37
<212> TYPE: DNA
<213> ORGANISM: Solidago canadensis

<400> SEQUENCE: 7
gaaataaacg cccagtacga aaaagtacag ctctacc                                      37

<210> SEQ ID NO 8
<211> LENGTH: 35
<212> TYPE: DNA
<213> ORGANISM: Solidago canadensis

<400> SEQUENCE: 8
cgtgatcgac atgctggcga agaatgacga caacc                                        35

<210> SEQ ID NO 9
<211> LENGTH: 35
<212> TYPE: DNA
<213> ORGANISM: Solidago canadensis

<400> SEQUENCE: 9
ggttgtcgtc attcttcgcc agcatgtcga tcacg                                        35

<210> SEQ ID NO 10
<211> LENGTH: 36
<212> TYPE: DNA
<213> ORGANISM: Solidago canadensis

<400> SEQUENCE: 10
gcgtgatcga catgctgctg aagaatgacg acaacc                                       36

<210> SEQ ID NO 11
<211> LENGTH: 36
<212> TYPE: DNA
<213> ORGANISM: Solidago canadensis

<400> SEQUENCE: 11
ggttgtcgtc attcttcagc agcatgtcga tcacgc                                       36

<210> SEQ ID NO 12
<211> LENGTH: 33
<212> TYPE: DNA
<213> ORGANISM: Solidago canadensis

<400> SEQUENCE: 12
```

-continued gtgatcgaca tgctgttcaa gaatgacgac aac                                33

<210> SEQ ID NO 13
<211> LENGTH: 33
<212> TYPE: DNA
<213> ORGANISM: Solidago canadensis

<400> SEQUENCE: 13
gttgtcgtca ttcttgaaca gcatgtcgat cac                                33

<210> SEQ ID NO 14
<211> LENGTH: 34
<212> TYPE: DNA
<213> ORGANISM: Solidago canadensis

<400> SEQUENCE: 14
gaatctgacg ggtggcagca aaatgctgac gacg                               34

<210> SEQ ID NO 15
<211> LENGTH: 34
<212> TYPE: DNA
<213> ORGANISM: Solidago canadensis

<400> SEQUENCE: 15
cgtcgtcagc attttgctgc cacccgtcag attc                               34

<210> SEQ ID NO 16
<211> LENGTH: 34
<212> TYPE: DNA
<213> ORGANISM: Solidago canadensis

<400> SEQUENCE: 16
gaatctgacg ggtggcggca aaatgctgac gacg                               34

<210> SEQ ID NO 17
<211> LENGTH: 34
<212> TYPE: DNA
<213> ORGANISM: Solidago canadensis

<400> SEQUENCE: 17
cgtcgtcagc attttgccgc cacccgtcag attc                               34

<210> SEQ ID NO 18
<211> LENGTH: 34
<212> TYPE: DNA
<213> ORGANISM: Solidago canadensis

<400> SEQUENCE: 18
gaatctgacg ggtggcgcga aaatgctgac gacg                               34

<210> SEQ ID NO 19
<211> LENGTH: 34
<212> TYPE: DNA
<213> ORGANISM: Solidago canadensis

<400> SEQUENCE: 19
cgtcgtcagc attttcgcgc cacccgtcag attc                               34

<210> SEQ ID NO 20
<211> LENGTH: 34
<212> TYPE: DNA
<213> ORGANISM: Solidago canadensis

<400> SEQUENCE: 20
gaatctgacg ggtggcgtga aaatgctgac gacg            34

<210> SEQ ID NO 21
<211> LENGTH: 34
<212> TYPE: DNA
<213> ORGANISM: Solidago canadensis

<400> SEQUENCE: 21
cgtcgtcagc attttcacgc cacccgtcag attc            34

<210> SEQ ID NO 22
<211> LENGTH: 34
<212> TYPE: DNA
<213> ORGANISM: Solidago canadensis

<400> SEQUENCE: 22
gaatctgacg ggtggcatta aaatgctgac gacg            34

<210> SEQ ID NO 23
<211> LENGTH: 34
<212> TYPE: DNA
<213> ORGANISM: Solidago canadensis

<400> SEQUENCE: 23
cgtcgtcagc attttaatgc cacccgtcag attc            34

<210> SEQ ID NO 24
<211> LENGTH: 34
<212> TYPE: DNA
<213> ORGANISM: Solidago canadensis

<400> SEQUENCE: 24
gaatctgacg ggtggcctga aaatgctgac gacg            34

<210> SEQ ID NO 25
<211> LENGTH: 34
<212> TYPE: DNA
<213> ORGANISM: Solidago canadensis

<400> SEQUENCE: 25
cgtcgtcagc attttcaggc cacccgtcag attc            34

<210> SEQ ID NO 26
<211> LENGTH: 34
<212> TYPE: DNA
<213> ORGANISM: Solidago canadensis

<400> SEQUENCE: 26
gaatctgacg ggtggcttta aaatgctgac gacg            34

<210> SEQ ID NO 27
<211> LENGTH: 34
<212> TYPE: DNA
<213> ORGANISM: Solidago canadensis

<400> SEQUENCE: 27
cgtcgtcagc attttaaagc cacccgtcag attc            34

<210> SEQ ID NO 28
<211> LENGTH: 29
<212> TYPE: DNA
<213> ORGANISM: Solidago canadensis

```
<400> SEQUENCE: 28
ctgacgggtg gctggaaaat gctgacgac                                              29

<210> SEQ ID NO 29
<211> LENGTH: 29
<212> TYPE: DNA
<213> ORGANISM: Solidago canadensis

<400> SEQUENCE: 29
gtcgtcagca ttttccagcc acccgtcag                                              29
```